(12) United States Patent
Lingwood et al.

(10) Patent No.: US 6,835,710 B1
(45) Date of Patent: Dec. 28, 2004

(54) VEROTOXIN PHARMACEUTICAL COMPOSITIONS AND MEDICAL TREATMENTS THEREWITH

(75) Inventors: Clifford A. Lingwood, Toronto (CA); Hannah Farkas-Himsley, deceased, late of Toronto (CA); by Ruth Geva, legal representative, Jerusalem (CA); by Leorah Kroyanker, legal representative, Jerusalem (CA); Richard Hill, Toronto (CA)

(73) Assignees: HSC Research & Development Limited Partnership, Toronto (CA); Ontario Cancer Institute, Toronto (CA)

( * ) Notice: Subject to any disclaimer, the term of this patent is extended or adjusted under 35 U.S.C. 154(b) by 218 days.

(21) Appl. No.: 09/632,056

(22) Filed: Aug. 3, 2000

Related U.S. Application Data

(63) Continuation of application No. 08/902,247, filed on Jul. 29, 1997, now Pat. No. 6,228,370, which is a continuation of application No. 08/386,957, filed on Feb. 10, 1995, now abandoned.

(30) Foreign Application Priority Data

Feb. 22, 1994 (CA) ............................................. 2116179

(51) Int. Cl.[7] .............................................. C07K 14/00
(52) U.S. Cl. ..................... 514/2; 424/236.4; 424/241.1; 424/94.1
(58) Field of Search ......................... 514/2; 424/236.1, 424/241.1, 94.1

(56) References Cited

U.S. PATENT DOCUMENTS

| | | | |
|---|---|---|---|
| 5,801,145 A | 9/1998 | Gariepy | 514/12 |
| 5,968,894 A | * 10/1999 | Lingwood et al. | 514/2 |
| 6,228,370 B1 | * 5/2001 | Lingwood et al. | 424/236.1 |

OTHER PUBLICATIONS

Farkas–Himsley, et al: "Bacterial Proteinaceous Products (Bacteriocins) as Cytotoxic Agents of Neoplasia", *Cancer Research*, vol. 36, pp. 3562–3567 (Oct. 1976).

Hill, et al: "Further studies of the Action of a Partially Purified Bacteriocin against a Murine Fibrosarcoma", *Cancer Research*, vol. 51, pp. 1359–1365 (Mar. 1, 1991).

Karmali: "Infection by Verocytotoxin–Producing *Escherichia coli*", *Clinical Microbiology Reviews*, vol. 2, No. 1, pp. 15–38 (Jan. 1989).

Riley, et al: "Hemorrhagic Colitis Associated with a Rare *Escherichia coli* Serotype", *The New England Journal of Medicine*, vol. 308, No. 12, pp. 681–685 (Mar. 24, 1983).

Lingwood: "Verotoxin and Their Glycolipid Receptors", *Advances in Lipid Research*, vol. 25, pp. 189–211 (1993).

van de Kar, et al: Tumor Necrosis Factor and Interleukin–1 Induce Expression of the Verocytotoxin Receptor Globotriaosylceramide on Human Endothelial Cells: Implications.

Obrig, et al: "Endothelial Heterogeneity in Shiga Toxin Receptors and Responses", *The Journal of Biological Chemistry*, vol. 268, No. 21, pp. 15484–15488 (Jul. 25, 1993).

Lingwood: "Verotoxin–Binding in Human Renal Sections", *Nephron*, vol. 66, pp. 21–28 (1994).

Cohen, et al: "Expression of Glycolipid Receptors to Shiga–like Toxin on Human B Lymphocytes: a Mechanism for the failure of long–lived antibody response to dysenteric disease", *International Immunology*, vol. 2, No. 1, pp. 1–8 (1990).

Gregory, et al: "Identification of a Subset of Normal B Cells with a Burkitt's Lymphoma (BL)–Like Phenotype", *The Journal of Immunology*, vol. 139, No. 1, pp. 313–318 (Jul. 1, 1987).

Maloney, et al: "CD19 has a Potential CD77 (Globotriaosyl Ceramide)–binding Site with Sequence Similiarity to Verotoxin B–subunits: Implications of Molecular Mimicry for B Cell Adhesion and Enterohemorrhagic *Escherichia coli* Pathogenesis", *J. Exp. Med.*, vol. 180, pp. 191–201 (Jul. 1994).

Maloney, et al: "Interaction of Verotoxins with Glycosphingolipids", *Trends in Glycoscience and Glycotechnology*, vol. 5, No. 21, pp. 23–31 (Jan. 1993).

Li, et al: "Accumulation of Globotriaosylceramide in a case of Leiomyosarcoma", *Biochemistry J.*, vol. 240, pp. 925–927 (1986).

Mannori, et al: Role of Glycolipids in the Metastatic Process: Characteristics of Neutral Glycolipids in Clones with Different Metastatic Potentials Isolated from a Murine Fibrosarcoma.

Ohyama, et al: "Changes in Glycolipid Expression in Human Testicular Tumor", *Intl. J. Cancer*, vol. 45, pp. 1040–1044 (1990).

Naiki, et al: "Human Erythrocyte P and P[k] Blood Group Antigens: Identification as Glycosphingolipids", *Biochemical and Biophysical Research Communications*, vol. 60, No. 3, pp. 1105–1111 (1974).

(List continued on next page.)

*Primary Examiner*—Karen Cochrane Carlson
(74) *Attorney, Agent, or Firm*—Lahive & Cockfield, LLP; Giulio A. DeConti, Jr.; Cynthia M. Soroos

(57) ABSTRACT

Pharmaceutical compositions comprising known verotoxins, particularly, verotoxin 1, have been found to be useful in the treatment of mammalian neoplasia, particularly, ovarian cancer and skin cancer. Surprisingly, although verotoxin 1 has previously been shown to have anti-neoplastic activity in vitro, non-lethal doses of verotoxin 1 have been shown to be therapeutically anti-neoplastic in vivo.

5 Claims, 6 Drawing Sheets

OTHER PUBLICATIONS

Pallesen, et al: "Distribution of the Burkitt's Lymphoma-associated Antigen (BLA) in Normal Human Tissue and Malignant Lymphoma as Defined by Immunohistological Staining with Monoclonal Antibody 38.13", *J. Cancer Res. Clin. Oncol.*, vol. 113, pp. 67–86 (1987).

Kasai, et al: "Tissue Distribution of the $P^k$ Antigen as Determined by a Monoclonal Antibody", *Journal of Immunogenetics*, vol. 12, pp. 213–220 (1985).

Pudymaitis, et al: "Susceptibility to Verotoxin as a Function of the Cell Cycle", *Journal of Cellular Physiology*, vol. 150, pp. 632–639 (1992).

Lingwood, et al: "Glycolipid Modification of α2 Interferon Binding", *Biochem, J.*, vol. 283, pp. 25–26 (1992).

Sandvig, et al: "Retrograde Transport of Endocytosed Shiga Toxin to the Endoplasmic Reticulum", *Nature*, vol. 358, pp. 510–512 (Aug. 6, 1992).

Mangeney, et al: "Apoptosis induced in Burkitt's lymphoma cells via $Gb_3$/CD77, a glycolipid antigen", *Cancer Res.*, vol. 53, pp. 5314–5319 (1993).

Costello, et al. "Human cerebral endothelium; Isolation and characterization of cell derived from microvessels of non–neoplastic and malignant glial tissue" *J. Neuro Oncol.*, vol. 8, pp. 231–243 (1990).

Pintus, et al. "Endothelial cell growth supplement: a cell cloning factor that promotes the growth of mono–clonal antibody producing hydridoma cells", *J. Immunological Methods*, vol. 61, pp. 195–200 (1983).

Rutka, et al. "Characterization of normal human brain cultures: Evidence for the outgrowth of leptomeningeal cells", *Laboratory Investigation*; vol. 55, pp. 71–85 (1986).

Sandvig et al. "Toxin Induced Cell Lysis: Protection by 3–Methyladenine and Cycloheximide" *EXP CELL*, vol. 200, pp. 253–262 (1992).

Head, et al.: "Purification and characterization of verocytotoxin 2", *FEMS Microbiology Letters*, 51, pp. 211–216 (1988).

Ramotar, et al. "Characterization of Shiga–like toxin I B subunit purified from overproducing clones of the SLT–I B cistron", *Biochem. J.*, vol. 272, pp. 805–811 (1990).

\* cited by examiner

Fig. 2 skov3
skovc
skovlb 3-day treatment of astrocytoma lines with VT1,

VEROTOXIN PHARMACEUTICAL COMPOSITIONS AND MEDICAL TREATMENTS THEREWITH

This application is a continuation application of Ser. No. 08/902,247 filed on Jul. 29, 1997 now U.S. Pat. No. 6,228, 370. Issuing, which in turn is a continuation application of Ser. No. 08/386,957 filed on Feb. 10, 1995 now abandoned. The contents of all of the aforementioned application(s) are hereby incorporated by reference.

FIELD OF THE INVENTION

This invention relates to verotoxin pharmaceutical compositions and to methods of treating mammalian neoplasia, particularly, ovarian and skin cancers, therewith.

BACKGROUND OF THE INVENTION

Bacteriocins are bacterial proteins produced to prevent the growth of competing microorganisms in a particular biological niche. A preparation of bacteriocin from a particular strain of $E.\ coli$ ($HSC_{10}$) has long been shown to have anti-neoplastic activity against a variety of human tumour cell lines in vitro (1,2). This preparation, previously referred to as PPB (partially purified bacteriocin (2)) or ACP (anti-cancer proteins (2)) was also effective in a murine tumour model, of preventing metastases to the lung (2).

Verotoxins, also known as SHIGA-like toxins, comprise a family known as Verotoxin 1, Verotoxin 2, Verotoxin 2c and Verotoxin 2e of subunit toxins elaborated by some strains of $E.\ coli$ (3). These toxins are involved in the etiology of the hemolytic uremic syndrome (3,4) and haemorrhagic colitis (5). Cell cytotoxicity is mediated via the binding of the B subunit of the holotoxin to the receptor glycolipid, globotriaosylceramide, in sensitive cells (6).

The verotoxin family of $E\ coli$ elaborated toxins bind to the globo series glycolipid globotriaosylceramide and require terminal gal $\alpha$-1-4 gal residue for binding. In addition, VT2e, the pig edema disease toxin, recognizes globotetraosylceramide ($Gb_4$) containing an additional $\beta$ 1-3 linked galNac residue. These glycolipids are the functional receptors for these toxins since incorporation of the glycolipid into receptor negative cells renders the recipient cells sensitive to cytotoxicity. The toxins inhibit protein synthesis via the A subunit—an N-glycanase which removes a specific adenine base in the 28S RNA of the 60S RNA ribosomal subunit. However, the specific cytotoxicity and specific activity is a function of the B subunit. In an in vitro translation system, the verotoxin A subunit is the most potent inhibitor of protein synthesis yet described, being effective at a concentration of about 8 pM. In the rabbit model of verocytotoxemia, pathology and toxin targeting is restricted to tissues which contain the glycolipid receptor and these comprise endothelial cells of a subset of the blood vasculature. Verotoxins have been strongly implicated as the etiological agents for hemolytic uremic syndrome and haemorrhagic colitis, microangiopathies of the glomerular or gastrointestinal capillaries respectively. Human umbilical vein endothelial cells (HUVEC) are sensitive to verotoxin but this sensitivity is variable according to cell line. Human adult renal endothelial cells are exquisitely sensitive to verotoxin in vitro and express a correspondingly high level of $Gb_3$. However, HUS is primarily a disease of children under three and the elderly, following gastrointestinal VTEC infection. It has been shown that receptors for verotoxin are present in the glomeruli of infants under this age but are not expressed in the glomeruli of normal adults. HUVEC can be sensitized to the effect of verotoxin by pretreatment by tumour necrosis factor which results in a specific elevation of $Gb_3$ synthesis (7,8). Human renal endothelial cells on the other hand, although they express high levels of $Gb_3$ in culture, cannot be stimulated to increase $Gb_3$ synthesis (8). It has been suggested that the transition from renal tissue to primary endothelial cell culture in vitro results in the maximum stimulation of $Gb_3$ synthesis from a zero background (9). We therefore suspect that HUS in the elderly is the result of verotoxemia and a concomitant stimulation of renal endothelial cell $Gb_3$ synthesis by some other factor, e.g. LPS stimulation of serum $\alpha$ TNF. Thus under these conditions, the majority of individuals (excepting the very young) would not be liable to VT induced renal pathology following systemic verotoxemia.

It has also shown that the verotoxin targets a subpopulation of human B cells in vitro (10). These $Gb_3$ containing B cells are found within the germinal centres of lymph nodes (11). It has been proposed that $Gb_3$ may be involved in a germinal centre homing by CD19 positive B cells (12) and that $Gb_3$ may be involved in the mechanisms of antigen presentation (13).

Elevated levels of $Gb_3$ have been associated with several other human tumours (14–16), but ovarian tumours have not been previously investigated. $Gb_3$ is the $p^k$ blood group antigen (17). Tissue surveys using anti-$p^k$ antisera have shown that human ovaries do not express this glycolipid (18, 19).

Sensitivity to VT1 cytotoxicity in vitro has been shown to be a function of cell growth, the stationary phase cells being refractile to cytotoxicity (20). The sequence homology between the receptor binding B subunit and the human $\alpha$2-interferon receptor and the B cell marker CD19 suggests that expression of $Gb_3$ is involved in the mechanism of $\alpha$2-interferon and CD19 signal transduction (12). On surface ligation, $Gb_3$ has been shown to undergo a retrograde intracellular transport via the rough endoplasmic reticulum to the nuclear membrane (21).

Reference List

The present specification refers to the following publications, each of which is incorporated herein by reference:

1. Farkas-Himsley, H. and R. Cheung. Bacterial Proteinaceous Products (bacteriocins as cytotoxic agents of neoplasia). *Cancer Res.* 36:3561–3567, (1976).
2. Hill, R. P. and H. Farkas-Himsley. Further studies of the action of a partially purified bacteriocin against a murine fibrosarcoma. *Cancer Res.* 51:1359–1365 (1991).
3. Karmali, M. A. Infection by Verocytotoxin-producing *Escherichia coli. Clin. Microbiol. Rev.* 2:15–38 (1989).
4. Karmali, M. A., M. Petric, C. Lim, P. C. Fleming, G. S. Arbus and H. Lior, 1985. The association between hemolytic uremic syndrome and infection by Verotoxin-producing *Escherichia coli*, J. Infect. Dis. 151:775.
5. Riley, L. W., R. S. Remis, S. D. Helgerson, H. B. McGee, J. G. Wells, B. R. Davis, R. J. Hebert, E. S. Olcott, L. M. Johnson, N. T. Hargrett, P. A. Blake and M. C. Cohen. Haemorrhagic colitis associated with a rare *Escherichia coli* serotype. *N. Engl. J. Med.* 308:681 (1983).
6. Lingwood, C. A., Advances in Lipid Research. R. Bell, Y. A. Hannun and A. M. Jr. *Academic Press.* 25:189–211 (1993).
7. van de Kar, N. C. A. J., L. A. H. Monnens, M. Karmali and V. W. M. van Hinsbergh. Tumour necrosis factor and interleukin-1 induce expression of the verotoxin receptor globotriaosyl ceramide on human endothelial cells. Implications for the pathogenesis of the Hemolytic Uremic Syndrome. *Blood.* 80:2755, (1992).
8. Obrig T., C. Louise, C. Lingwood, B. Boyd, L. Barley-Maloney and T. Daniel. Endothelial heterogeneity in Shiga toxin receptors and responses. *J. Biol. Chem.* 268:15484–15488 (1993).
9. Lingwood, C. A. Verotoxin-binding in human renal sections. *Nephron.* 66:21–28 (1994).
10. Cohen, A., V. Madrid-Marina, Z. Estrov, M. Freedman, C. A. Lingwood and H. M. Dosch. Expression of glycolipid receptors to Shiga-like toxin on human B lymphocytes: a mechanism for the failure of long-lived antibody response to dysenteric disease. *Int. Immunol.* 2:1–8 (1990).
11. Gregory, C. D., T. Turz, C. F. Edwards, C. Tetaud, M. Talbot, B. Caillou, A. B. Rickenson and M. Lipinski. 1987. Identification of a subset of normal B cells with a Burkitt's lymphoma (BL)-like phenotype. *J. Immunol.* 139:313–318 (1987).
12. Maloney, M. D. and C. A. Lingwood, CD19 has a potential CD77 (globotriaosyl ceramide) binding site with sequence similarity to verotoxin B-subunits: Implications of molecular mimicry for B cell adhesion and enterohemorrhagic *E. coli* pathogenesis. *J. Exp. Med.* 180: 191–201, (1994).
13. Maloney, M. and C. Lingwood. Interaction of verotoxins with glycosphingolipids. *TIGG.* 5:23–31 (1993).
14. Li, S. C., S. K. Kundu, R. Degasperi and Y. T. Li. Accumulation of globotriaosylceramide in a case of leiomyosarcoma. *Biochem. J.* 240:925–927 (1986).
15. Mannori G., O. Cecconi, G. Mugnai and S. Ruggieri. Role of glycolipids in the metastatic process: Characteristics neutral glycolipids in clones with different metastatic potentials isolated from a murine fibrosarcoma cell line. *Int. J. Cancer.* 45:984–988 (1990).
16. Ohyama, C., Y. Fukushi, M. Satoh, S. Saitoh, S. Orikasa, E. Nudelman, M. Straud and S. I. Hakomori. Changes in glycolipid expression in human testicular tumours. *Int. J. Cancer.* 45:1040–1044, (1990).
17. Naiki, M. and D. M. Marcus. Human erythrocyte P and $P^k$ blood group antigens: Identification as glycosphingolipids. *Biochem. Biophys. Res. Comm.* 60:1105–1111, (1974).
18. Pallesen, G. and J. Zeuthen. Distribution of the Burkitt's-lymphoma-associated antigen (BLA) in normal human tissue and malignant lymphoma as defined by immunohistological staining with monoclonal antibody 38:13. *J. Cancer Res. Clin. Oncol.* 113:78–86 (1987).
19. Kasai, K., J. Galton, P. Terasaki, A. Wakisaka, M. Kawahara, T. Root and S. I. Hakomori. Tissue distribution of the Pk antigen as determined by a monoclonal antibody. *J. Immunogenet.* 12:213 (1985).
20. Pudymaitis, A. and C. A. Lingwood. Susceptibility to verotoxin as a function of the cell cycle. *J. Cell Physiol.* 150:632–639 (1992).
21. Sandvig, K., O. Garred, K. Prydz, J. Kozlov, S. Hansen and B. van Deurs. Retrograde transport of endocytosed Shiga toxin to the endoplasmic reticulum. *Nature.* 358:510–512 (1992).

Although anti-neoplastic effects of bacterial z:) preparations have been known for over twenty years, the neoplastic effect of verotoxin per se has, to-date, remained unknown. As a result of extensive investigations, we have discovered that verotoxin, particularly Verotoxin 1, is an active component within the ACP and that purified Verotoxin 1 has potent anti-neoplasia effect in vitro and in vivo. Most surprisingly, we have found effective in vivo anti-cancer treatments of human beings commensurate with non-toxic administered dosages.

SUMMARY OF THE INVENTION

It is an object of the present invention to provide a pharmaceutical composition for the treatment of mammalian neoplasia and, particularly, skin cancer and ovarian cancer.

It is a further object of the present invention to provide a method of treating mammalian neoplasia, particularly, skin, brain and ovarian cancers.

Accordingly, in one aspect the invention provides a pharmaceutical composition for the treatment of mammalian neoplasia comprising a non-lethal anti-neoplasia effective amount of a verotoxin, preferably, verotoxin 1, and a suitable pharmaceutically acceptable diluent, adjuvant or carrier therefor.

The invention preferably provides a pharmaceutical composition and method of treatment for mammalian skin cancers, brain cancers and ovarian cancer.

In a further aspect the invention provides a process for the manufacture of a pharmaceutical composition for the treatment of mammalian neoplasia, said process comprising admixing verotoxin with a pharmaceutically acceptable carrier, adjuvant or diluent therefor.

The present invention provides selective, specific cancer treatments wherein verotoxin selectively binds with $Gb_3$ in $Gb_3$-containing cells. This is in contrast to the use of broad spectrum anti-neoplastic agents such as most chemotherapeutic agents, in that non-$Gb_3$ containing cells are not affected by verotoxin. The present invention thus provides a most beneficial, cell-selective, therapeutic treatment.

The treatment is of value against cutaneous T-cell lymphomas, particularly, Mycosis Fungoides, sezary syndrome and related cutaneous disease lymphomatoid papilosis. For example, Mycosis fungoides lesions in humans have been cleared without any observed adverse systemic effects by the application of VT1 (5 ng in 2 ml. solution) by interdermal injection in patients.

In a further aspect, the invention provides a method of treating mammalian neoplasia comprising treating said mammal with a non-lethal anti-neoplasia effective amount of a verotoxin, preferably Verotoxin 1.

The verotoxin may be administered to the patient by methods well-known in the art, namely, intravenously, intraarterially, topically, subcutaneously, by ingestion, intramuscular injection, inhalation, and the like, as is appropriately suitable to the disease. For treatment of a skin cancer, sub-cutaneous application is preferred.

In the practice of the present invention, Verotoxin 1 has been injected intramuscularly into a patient with advanced ovarian carcinoma. No adverse affects were monitored on lymphocyte or renal function and a serum tumour marker was found to continue to rise when the patient was treated with relatively high doses of Verotoxin 1. This tumour was refractory to all conventional cancer therapies. No effect was found on hemoglobin levels.

The verotoxin is, typically, administered in a suitable vehicle in which the active verotoxin ingredient is either dissolved or suspended in a liquid, such as serum to permit the verotoxin to be delivered for example, in one aspect from the bloodstream or in an alternative aspect sub-cutaneously to the neoplastic cells. Alternative, for example, solutions are, typically, alcohol solutions, dimethyl sulfoxide solutions, or aqueous solutions containing, for example, polyethylene glycol containing, for example, polyethylene glycol 400, Cremophor-EL or Cyclodextrin. Such vehicles are well-known in the art, and useful for the purpose of delivering a pharmaceutical to the site of action.

Several multi-drug resistant cell lines were found to be hypersensitive to Verotoxin 1. For example, multidrug resistant ovarian cancer cell lines SKVLB and SKOVLC were more sensitive to VT cytotoxicity than corresponding non-multidrug resistant ovarian cancer cell line SKOV3. Such an observation indicates the possible beneficial effect for patients bearing the SKVLB cell line cancer than those with the SKOV3 cell line under VT treatment. Further, our observed binding of VT1 to the lumen of blood vessels which vascularize the tumour mass, in addition to the tumour cells per se, may result in an anti-angiogenic effect to augment the direct anti-neoplastic effect of verotoxin.

BRIEF DESCRIPTION OF THE DRAWINGS

In order that the invention may be better understood preferred embodiments will now be described, by way of example only, with reference to the accompanying drawings wherein:

FIG. 2 shows the viability of selected ovarian and breast tumour cell lines to verotoxin concentration;

and FIG. 9 represents the results of a three-day treatment of several human astrocytoma cell lines with VT1.

DETAILED DESCRIPTION OF THE INVENTION

Experimental

Figure 1:
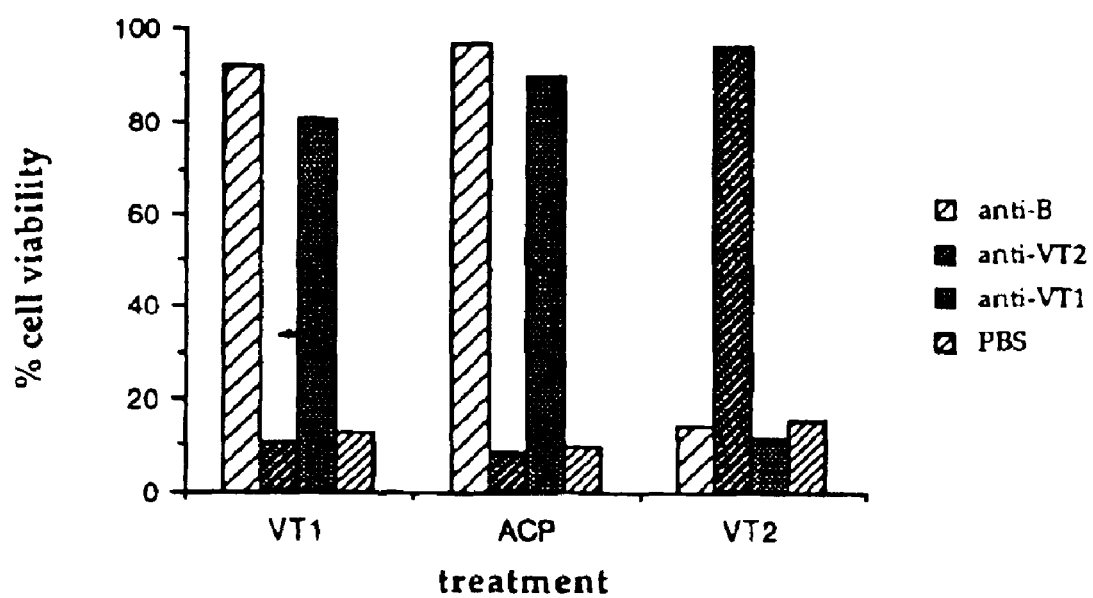
FIG. 1 shows the selective neutralization of ACP cytotoxicity by anti VT1 and or anti VT1 B subunit but not by anti VT2 antibodies as determined by cell density measurement after 48 hours.

The isolation and purification of verotoxins VT1, VT2 and VT2c have been earlier described.

Verotoxin 1 was prepared genetically from the high expression recombinant *E. coli* pJB28, *J. Bacteriol* 166:375 and 169:4313. The generally protein purification procedure described in *FEMS Microbiol. Lett.* 41:63, was followed.

Verotoxin 2 was obtained from R82, *Infect. Immun.* 56:1926–1933; (1988); and purified according to *FEMS Microbiol. Lett.* 48:379–383 (1987).

Verotoxin 2c was obtained from a clinical strain E32511 and purified according to *FEMS Microbiol. Lett.* 51:211–216 (1988).

Purification of VT1 from JB28

Pellet Preparation may be Conducted as Follows:
1. Prepare 6×1 L LB broth in 3×5 L jugs (media) and autoclave.
   Add carbenicillin to give a 100 µg/ml final conc. when cool.
2. Seed at least 6 ml of penassay (tubes in cold room)+100 µg/ml carbenicillin with JB28 and incubate O/N @37° C.
3. Seed jugs (1 ml seed/liter broth) next morning and incubate for 24 hours at 37° C. at 200 rpm (vigorous shaking).
4. Spin down bugs at 9K for 15 min. at 4° C. and scrape pellet into a freezer bag for future use. Freeze at −70° C.

Preparation of Crude Toxin Extract:
1. Retrieve pellet and dump into beaker. Resuspend in 400 ml of PBS containing 0.1 mg/ml polymyxin B, 50 mg PMSF using a blender. Blend thoroughly then sonicate on ice for—1 minute to disperse further.
2. Incubate in shaking incubator, 200 rpm, or with vigorous stirring @37° C. for 1 hour.
3. Spin down cells @9K for 15 minutes.
4. Pour off supernatant and keep. Resuspend pellet in 400 ml PBS with 0.1 mg/ml polymyxin B and PMSF. Blend and sonicate as before.
5. Incubate with vigorous shaking/stirring at 37° C. for 1 hour.
6. Spin at 10K for 15 minutes and save supernatant.
7. The supernatants should be quite yellow and the bacterial pellet should become more fine and diffuse with each extraction step.
8. Filter the combined supernatants through Whatman filter paper than through a glass fibre filter to clarify. This step is optional, but will greatly speed the concentration step.
9. Amicon the combined supernatants at 70 psi (max.) using a YM10 membrane (takes about 200 hours) to concentrate to <50 ml.

Chromatography:
Hydroxylapatite
1. Equilibrate hydroxylapatite column with 10 mM K or Na phosphate (several column volumes).
2. Load sample and wash with equilibration buffer until absorbance of effluent is negligible.
3. Add 2 column volumes (150 ml) of 100 mM K phosphate (until yellow-coloured fractions emerge) and collect 3 ml fractions.
4. Wash column with 500 mM K phosphate and re-equilibrate with 10 mM K phosphate. Add 0.05% sodium azide.

Chromatofocussing
5. Measure fractions ($A_{280}$) and Pool peak fractions from HA.
6. Dialyse against 2 L 0.025M imidazole-HCl pH 7.4 O/N. Also equilibrate the chromatofocussing column O/N with the same (300 ml).
7. Load sample and follow with 400 ml polybuffer-HCl pH 5.0 (50 ml polybuffer 74+350 ml $dH_2O$, a 1:7 dilution, −pH to 5.0 with HCl). NOTE: make sure the sample is equilibrated to the temperature that the column will be run at (usually room temperature) prior to loading. If the column is to be run at 4° then buffers must be pH'd at 4° C. and the column equilibrated at this temperature.
8. Collect 1 ml fractions and test them for $A_{280}$ and pH.
9. Plot the $A_{280}$ and pool peak fractions at about pH 6.8 for VT-1 (pool side peaks separately).
10. Clean column with 100 ml 1M NaCl. if really dirty follow with 100 ml 1M HCl, but quickly equilibrate column with imidazole. Store column in 20% ethanol in 25 mM imidazole.

Cibachron Blue
11. Equilibrate cibachron blue with 10 mM Na phosphate buffer, pH 7.2 (100 ml).
12. Load sample directly from CF and follow with 60 ml of same buffer.
13. Elute with 0.5M NaCl in above buffer and collect fractions.
14. Test fractions for $A_{280}$ and cytotoxicity and pool appropriate ones.
15. Clean column with 25 ml each of 8M Urea in wash buffer and 1M NaCl in wash buffer.
16. Reequilibrate column with 10 mM phosphate containing 0.1% azide.
17. Dialyse peak fractions against wash buffer with one change.
18. Lyophilize and resuspend in 1 ml $dH_2O$.
19. Do protein assay and run SDS-PAGE to check purity.

Solutions:

HA column
potassium phosphate buffer (0.5 M stock)

17.42 g K$_2$HPO$_4$      up to 300 ml with dH2O
6.8 g KH$_2$PO$_4$      pH 7.2 with KOH
CF column
imidazole buffer 0.851 g/500 ml H$_2$O
pH 7.4 with HCl
CB column
sodium phosphate buffer (Wash buffer-WB)

0.71 g/500 ml Na$_2$HPO$_4$
pH 7.2 with HAc
degas

Elution buffer      Cleaning Buffers 2.922 g NaCl/100 ml WB      12.012 g Urea/25 ml WB
     1.461 g NaCl/25 ml WB

Purification of VT2 from R82

Pellet Preparation:
1. Prepare 3×2 L penassay broth (Antibiotic Meida 3, DIFCO; pH~7.0) in 3×5 L jugs and autoclave at 121° C. for 20 minutes. Allow broth to cool to room temperature before use.
2. Seed minimum 3×2 ml of penassay broth containing 75 μg/ml carbenicillin (Disodium salt, SIGMA) with R82 and incubate overnight at 37° C., with shaking.
3. Add 50 μg/ml carbenicillin to each of the 5 L jugs (from step 1). Seed each jug with 2 ml of seed (step 2) and incubate for 24 hours at 37° C. with shaking of approximately 120 rpm.
4. Heat incubator to 45° C. and incubate for 30 minutes.
5. Reduce temperature to 37° C. and incubate for another 3 hrs.
6. Spin down culture solution at 9,000×g for 15–20 min at 4° C. Discard supernatant and store pellets at −20° C.

Preparation of Crude Toxin Extract:
1. Resuspend pellets in 100 ml of PBS (phosphate buffered saline, OXOID; pH 7.3).
2. Add 0.3 mg/ml PMSF (phenylmethyl-sulfonyl fluoride, SIGMA) dissolved in 0.5 ml acetone to pellet solution. Let acetone evaporate. Sonicate on ice at highest output possible for 5 min or until an homogeneous solution is obtained.
3. Spin down cell at 9,000×g at 4° C. for 20 min. Discard pellets.
4. Concentrate supernatants using ultrafiltration (Model 8400 standard infiltration cell, AMICON) with N$_2$ no higher than 70 psi and using a 10,000 MW cutoff membrane filter (YM10 membrane, AMICON).
5. Using 12–14,000 MW cutoff tubing (SPECTRAPOR) (now and in all dialysis steps), dialyse toxin solution against 4 L of 10 mM potassium phosphate overnight, with stirring at 4° C.

Chromatography:
Hydroxylapatite (HA)
1. Equilibrate hydroxylapatite column (BSA binding capacity: 32 mg/g, approximately 113 ml volume; CALBIOCHEM (BEHRING DIAGNOSTICS)) with 2 column volumes of 10 mM potassium phosphate.
2. Load sample and follow with 1 column volume 10 mM potassium phosphate.
3. Add 2 column volumes of 200 mM potassium phosphate and collect 2 ml fractions. The fractions containing the toxin should be coloured differently from the other fractions.
4. Wash column with 1 column volume of 500 mM potassium phosphate and reequilibrate with 1 column volume of 10 mM potassium phosphate. Add azide to the top of the column for storage.

Chromatofocussing (CF)
5. Pool peak fractions from HA column either by colour or by cytotoxicity test on Vero cells (10-fold dilutions).
6. Dialyse pooled fractions against 4 L 0.025M Histidine-HCl pH 6.2 (SIGMA) overnight. Also equilibrate the chromatofocussing column (PBE (polybuffer exchanger) 94, 1.5 cm diameter, 57 ml volume; PHARMACIA) overnight with the same buffer (300 ml).
7. Loan sample and follow with 400 ml polybuffer-HCl pH 4.0 (50 ml polybuffer 74 (PHARMACIA)+350 ml dH$_2$O—pH to 4.0 with HCl).
8. Collect 2 ml fractions and test the pH of each fraction. Once the pH has dropped to 3.95, stop collecting fractions. Test the fractions using absorbance of 280 nm or by cytotoxicity on Vero cells (10-fold dilutions).
9. Pool peak fractions, and return pH to 7.0 using 1N NaOH.
10. Clean column with 200 ml 1M NaCl. If dirty follow with 100 ml 1M HCl, but quickly equilibrate column with 0.025M imidazole, otherwise equilibrate with 24% EtOH-H$_2$O.

Cibachron Blue (CB)
11. Equilibrate cibachron blue (2 cm diameter, 82 ml volume, PIERCE) with 100 ml of 10 mM sodium phosphate buffer (wash buffer).
12. Load sample and follow with 60 ml of wash buffer.
13. Elute with 0.5M NaCl in wash buffer and collect 2 ml fractions.
14. Test fractions for absorbance at 280 nm using the elution buffer as a blank and cytotoxicity on Vero cells and pool appropriate fractions.
15. Clean column with 25 ml each of 8M Urea in wash buffer and 1M NaCl in wash buffer.
16. Reequilibrate column with 100 ml or wash buffer and add azide to the top of the column for storage.
17. Dialyse peak fractions against 4 L 0.01M Tris-CL (pH 7.0, SIGMA).
18. Lyophilize sample and resuspend in 1–2 ml dH$_2$O (OPTIONAL).
19. Do protein assay (BCA Protein assay reagent, PIERCE) and rune SDS-PAGE gel (Schagger, H. and von Jagow, G.; Analytical Biochem 166, 368–379 (1987): 10% T table 2; first line table 3) to check purity.

Solutions:

HA Column potassium phosphate buffer (0.5M stock)
17.42 g K$_2$HPO$_4$      up to 300 ml with dH$_2$O
6.8 g KH$_2$PO$_4$      pH 7.2 with KOH
CF column Histidine buffer (0.025M)
2.0 g/500 ml H$_2$O
pH 6.2 with HCl
CB column Sodium phosphate buffer (Wash buffer-WB)
0.71 g/500 ml Na$_2$HPO$_4$
pH 7.2 with HAc
degas Elution buffer (0.5M)      Cleaning Buffers 2,922 g/NaCl/100 ml WB      12.01 g Urea/25 ml WB
     1.46 NaCl/25 ml WB -continued

| 0.01M Tris |
|---|
| 4.84 g Trizma Base<br>4 L $ddH_2O$<br>pH to 7.2 with HCl |

Purification of VT2c from E32511

Pellet Preparation:

1. Prepare 3×2 L penassay broth (Antibiotic Media 3, DIFCO; pH 7.0) in 3×5 L jugs and autoclave at 121° C. for 20 minutes. Allow broth to cool to room temperature before use.
2. Seed minimum 3×2 ml of penassay broth with E32511 and incubate overnight at 37° C.
3. Add 0.2 μg/ml Mitomycin C (1 ml of 0.4 mg/ml) (add 5 ml of $ddH_2O$ to the vial) to each of the 5 L jugs (from step 1). Seed each jug with 2 ml of seed (step 2) and incubate for 6 hrs at 37° C. with shaking of approximately 120 rpm. It is very important to stagger the incubation by about 45 min/flask because the toxin begins to deteriorate after 6 hour exposure to Mitomycin C.
4. Spin down culture solution at 9,000×g for 15–20 min at 4° C. Discard supernatant and store pellets at −20° C.

Preparation of Crude Toxin Extract:

1. Resuspend pellets in 150 ml of PBS (Phosphate buffered saline, OXOID; pH 7.3).
2. Add 0.3 mg/ml PMSF (phenylmethyl-sulfonyl fluoride, SIGMA) dissolved in 0.5 ml acetone to pellet solution. Let acetone evaporate. Sonicate on ice at highest output possible for 3 min or until an homogeneous solution is obtained.
3. Add 0.1 mg/ml polymyxin B sulphate (Aerosporin, BURROUGHS WELLCOME INC.; 500,000 units) to solution and incubate with gentle shaking at 37° C. for 1 hr.
4. Spin down cells at 9,000×g at 4° C. for 20 min (to remove all cells and cell debris from solution).
5. Decant supernatant and store at 4° C. Resuspend pellet in 75 ml PBS and add 0.1 mg/ml polymyxin B.
6. Incubate with gentle shaking at 37° C. for 1 hr.
7. Spin down cell at 9,000×g at 4° C. for 20 min and pool supernatants (from step 5). Discard pellets.

The next few steps should preferably be done at 4° C:

8. Add crystalline ammonium sulphate very slowly, with stirring to pooled supernatants to 30% saturation.
9. Let stir for 20 min and then remove precipitate by centrifugation (10000 g for 10 min).
10. Add crystalline ammonium sulphate very slowly, with stirring to pooled supernatants to 70% saturation.
11. Let stir for 20 min and then centrifuge at 10000 g for 10 min.
12. Resuspend pellet from step 11 in 15 ml of 0.01M Potassium phosphate buffer.
13. Using 12–14,000 MW cutoff tubing (SPECTRAPOR) (now and in all dialysis steps), dialyse toxin solution against 4 L of 10 mM potassium phosphate overnight, with stirring at 4° C.

Chromatography:

Hydroxylapatite (HA)

1. Equilibrate hydroxylapatite column (BSA binding capacity: 32 mg/g, approximately 113 ml volume; CALBIOCHEM (BEHRING DIAGNOSTICS)) with 2 column volumes of 10 mM potassium phosphate.
2. Load sample and follow with 1 column volume 10 mM potassium phosphate.
3. Add 2 column volumes of 100 mM–200 mM potassium phosphate and collect 2 ml fractions. The fractions containing the toxin should be coloured differently from the other fractions.
4. Wash column with 1 column volume of 500 mM potassium phosphate and reequilibrate with 1 column volume of 10 mM K phosphate. Add azide to the top of the column for storage.

Chromatofocussing (CF)

5. Pool peak fractions from HA column either by colour or by cytotoxicity test on Vero cells (10-fold dilutions).
6. Dialyse pooled fractions against 4 L 0.025M imidazole-HCl pH 7.4 (SIGMA) overnight. Also equilibrate the chromatofocussing column (PBE (polybuffer exchanger) 94, 1.5 cm diameter, 57 ml volume; PHARMACIA) overnight with the same buffer (300 ml).
7. Load sample and follow with 200 ml polybuffer-HCl pH 5.0 (25 ml polybuffer 74 (PHARMACIA)+175 ml $dH_2O$—pH to 5.0 with HCl).
8. Collect 2 ml fractions and test the pH of each fraction. Once the pH has dropped to 5.95, stop collecting fractions. Test the fractions for cytotoxicity on Vero cells (10-fold dilutions).
9. Pool peak fractions.
10. Clean column with 200 ml 1M NaCl. If really dirty follow with 100 ml 1M HCl, but quickly equilibrate column with 0.025M imidazole.

Cibachron Blue (CB)

11. Equilibrate cibachron blue (2 cm diameter, 82 ml volume, PIERCE) with 100 ml of 10 mM sodium phosphate buffer (wash buffer).
12. Load sample and follow with 60 ml of wash buffer.
13. Elute with 0.5M NaCl in wash buffer and collect 2 ml fractions.
14. Test fractions for absorbance at 280 nm using the elution buffer as a blank and cytotoxicity on Vero cells and pool appropriate fractions.
15. Clean column with 25 ml each of 8M Urea in wash buffer and 1M NaCl in wash buffer.
16. Reequilibrate column with 100 ml of wash buffer and add azide to the top of the column for storage.
17. Dialyse peak fractions against 4 L 0.01M Tris-CL (pH 7.0, SIGMA).
18. Lyophilize sample and resuspend in 1–2 ml $dH_2O$ (OPTIONAL).
19. Do protein assay (BCA Protein assay reagent, PIERCE) and run SDS-PAGE gel (Schagger, H. and von Jagow, G.; Analytical Biochem 166, 368–379 (1987): 10% T table 2; first line table 3) to check purity.

Solutions:

| | |
|---|---|
| HA column<br>potassium phosphate buffer (0.5 M stock) | |
| 17.42 g $K_2HPO_4$<br>6.8 g $KH_2PO_4$ | up to 300 ml with $dH_2O$<br>pH 7.2 with KOH |
| CF column<br>imidazole buffer (0.025 M) | |
| 0.851 g/500 ml $H_2O$<br>pH 7.4 with HCl | |
| CB column<br>sodium phosphate buffer (Wash buffer-WB) | |
| 0.71 g/500 ml $Na_2HPO_4$<br>pH 7.2 with HAc<br>degas | |

-continued

| Elution buffer | Cleaning buffers |
|---|---|
| 2.922 g NaCl/100 ml WB | 12.012 g Urea/25 ml WB |
| 0.01 M Tris | 1.461 g NaCl/25 ml WB |
| 4.84 g Trizma Base | |
| 4 L ddH$_2$O | |
| pH to 7.2 with HCl | |

Affinity Purification Verotoxins

500 μg globotriaosyl ceramide in 1 ml chloroform was mixed and dried with 1 g of dried celite. The chloroform was evaporated and the celite suspended in PBS and poured in a column. Crude polymyxin extract 20 ml (25 mg protein) the toxin producing E. coli was applied to the column and incubated at room temp for 15 mins. The column was washed with PBS and purified verotoxin eluted with 10 ml 1M Tris pH 9.6. The eluate was neutralized and dialysed. This method is applicable for purification of all verotoxins. (Boulanger, J., Huesca, M., Arab, S and Lingwood, C. A. "Universal method for the facile production of glycolipid/lipid matrices for the affinity purification of binding ligands" Anal Biochem 217: 1–6 [1994])

Preparation of Verotoxin 1 Doses

VT1 was purified from the E. coli strain as previously described which overexpresses the cloned toxin genes. The purified toxin was free of endotoxin contamination. The protein concentration of this batch of verotoxin was determined and the toxin aliquoted and stored at −70° C.

To prepare VT1 doses for patients, VT1 was diluted into injection grade sterile saline containing 0.2% v/v of the patient's own serum. 210 ul of sterile patient serum was added to 10 ml of sterile injection saline and 93.9 ml of purified VT1 (6.7 g/ml) added to give a final toxin concentration of 62.5 ng/ml or 12.5 ng per 0.2 ml. dose. The final toxin preparation was sterile-filtered using a 0.2 mm syringe filter and dispensed in 2 ml aliquots into 10 ml vials. One working vial may be stored at 4° C. and the remaining vials frozen until needed.

FITC labelling of VT1: FITC was added directly to VT1 (in a 1:1, w/w ratio) in 0.5M Na$_2$CO$_3$/NaHCO$_3$ conjugated buffer pH 9.5 and the mixture gently rotated for 1.2 hours at room temperature. Free FITC was removed by centricon.

Fluorescent Staining of Sections: Samples of surgically removed ovarian tumours were embedded in OCT compound, flash frozen in liquid nitrogen, and stored at −70° C. until use. Five μm sections of frozen sample were thawed, allowed to dry and stained with FITC-labelled VT1 in PBS (0.5 mg.ml) containing 0.1% BSA for 1 h at room temperature. Sections were extensively washed with PBS and mounted with mounting medium containing DABCO. Sections were observed under a Polyvar fluorescent microscope.

Fluorescent Staining of Cells: Cells growing on coverslips were washed once with PBS, fixed for 2 min at room temperature with 2% formalin rinsed with PBS twice and incubated with FITC-VT1 for 1 h at room temperature. The cells were washed 5 times with PBS, mounted with DABCO and observed under a Polyvar fluorescent microscope.

Quantification of VT1 antitumour activity: SKOV3 (drug sensitive human ovarian cell line), SKOVLC (SKOV3, resistant to Vincristine, and SKOVLB (SKOV3, resistant to Vinblastine) were each grown in α—MEM supplemented with 10% fetal calf-serum and tested for their sensitivity to VTs. Equal numbers of cells (approximately 1000 per/ml of media) were added to the wells of Linbro 98 well plate. 10-fold dilution of VTs were tested in triplicate and incubated for 48 h at 37° C. in a humidified atmosphere containing 5% CO$_2$. Cells were then fixed with 2% Formalin, stained with Crystal Violet, and read with ELISA plate reader.

To quantify the anticancer activity of VT1, SKOV3, SKOVLC, and SKOVLB (human ovarian cell line) were incubated with 10-fold dilution of VT1 for 48 h. SKOVLC & SKOVLB (drug resistant cell lines) are more sensitive to VT1 antitumour activity than SKOV3.

Preparation of $^{131}$I-VT1B

This material may be made by the following procedure.
1. Dissolve 20 mg of iodogen in 2.0 ml of chloroform (10 mg/ml). Make a 1:10 dilution by adding 0.25 ml of the 10 mg/ml solution to 2.25 ml chloroform (1 mg/ml).
2. Dispense 20 ul of this dilute solution into a clean, dry sterilized glass tub. Add 500 ul of chloroform and evaporate to dryness under N$_2$.
3. Add 1.5 mg. in 0.66 ml of VT1B subunit to the test tube.
4. Add 5 MCi of $^{131}$I sodium iodide in 100 ul. Allow labelling to proceed for 10 mins.
5. Wash a PD-10 column with 25 ml of Sodium Chloride Injection USP.
6. Dilute $^{131}$I-VT1B to 2.5 ml total volume with 1% HSA in Sodium Chloride Injection USP. Load onto PD-10 column. Elute column with 3.5 ml 1% HSA in saline.
7. Measure $^{131}$I activity of eluant and column to determine LE. Draw up pooled fractions into a syringe with spinal needle attached. Detach spinal needle and attach Millex GV filter.
8. Filter into a sterile 10 ml multidose vial. Note volume filtered and assay vial for $^{131}$I in dose calibrator. Calculate concentration.
9. Draw up 0.1 ml of $^{131}$I-VT1B and dispense 0.05 ml into each of two 5 ml sterile multidose vials (one for sterility test and one for pyrogen test). Vials already contain 2 ml saline (=1:50 dilution).
10. Determine RCP by PC (Whatman No. 1) in 85% MeOH and by size exclusion HPLC.
11. Conduct sterility and pyrogen tests.

FIG. 1 relates to the neutralization of ACP cytotoxicity by anti-VT. KHT cell monolayers were incubated with 35 ng/ml ACP from E.coli HSC$_{10}$, or 10 pg/ml VT1, VT2 or VT2c in the presence of monoclonal anti-VT1(PH1), monoclonal anti VT2 or polyclonal rabbit antiVT1 B subunit. The cells were incubated for 72 hours at 37° C. and viable adherent cells were detected by fixation and staining with crystal violet. Cytotoxity of VT1 and ACP was completely neutralized in the presence of anti VT1 or anti VT1B subunit (anti-VT2 serum had no effect).

Figure 2:
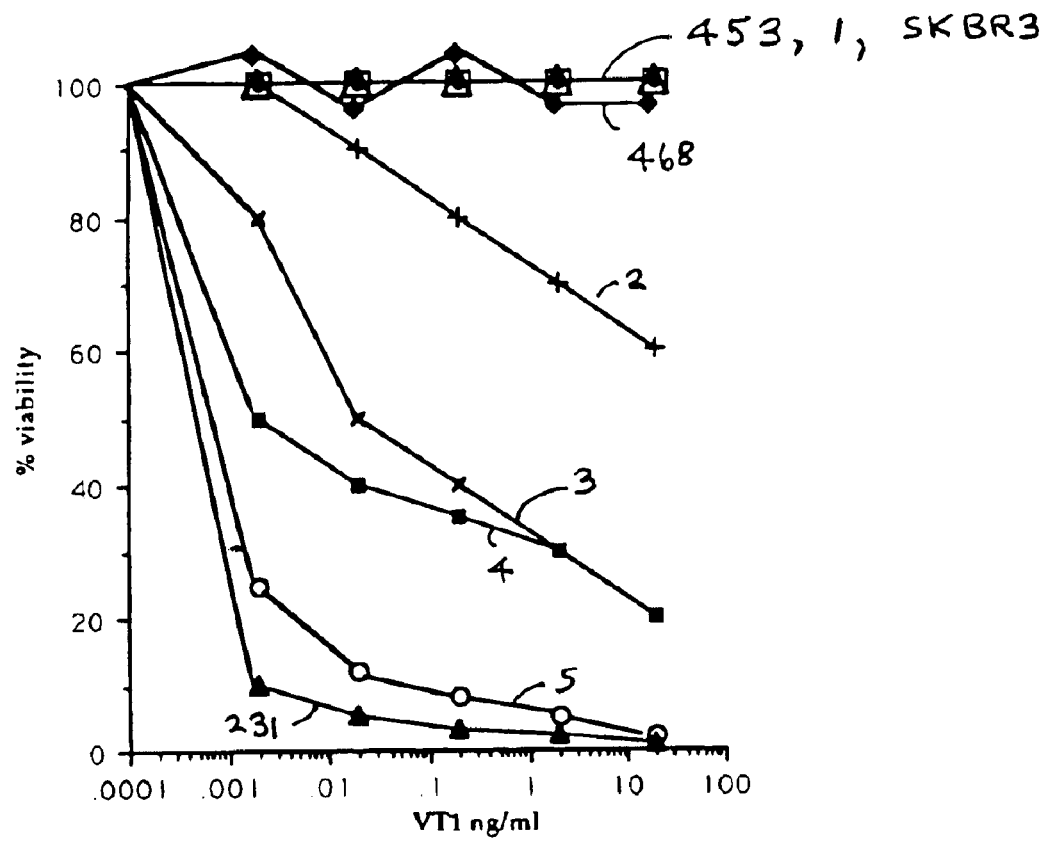

From measurement of the cytotoxic assay of ACP on vero cells (cells from Africa green monkey kidney that are very sensitive to verotoxin), relative to a pure VT1 standard, it was estimated that the ACP preparation contained 0.05% VT1. This concentration of purified VT1 was as effective as ACP in inhibiting the growth of various tumour cell lines in vitro (FIG. 2). Thus, VT1 mimics the anti-neoplastic effect of ACP in vitro. VT1 was tested for the ability to inhibit the metastases of KHT fibrosarcoma cells in the mouse model as had been previously reported for ACP. The equivalent dose of VT1 was as effective as ACP, reducing the number of lung metastases to background levels, following a primary subcutaneous tumour inoculum (Table 1).

TABLE 1

Response of KHT cells, growing as lung modules, to treatment with VT-1 or ACP.

| GP | TREATMENT | # OF MICE | # OF LUNG NODULES/MOUSE | MEAN | WT LOSS/ GAIN* |
|---|---|---|---|---|---|
| EXPT 1 | | | | | |
| 1 | Control | 9 | 34, 24, 39, 47, 28, 32, 26, 29, 34 | 32.6 | +5% |
| 2 | ACP-0.25 ug/mouse | 4 | 12, 31, 25, 15 | 20.8 | 0 |
| 3 | ACP-1.0 ug/mouse | 6 | 1, 2, 2, 5, 1 | 2.2 | 0** (1 death) |
| 4 | ACP-4 ug/mouse | 5 | 0, 0, 0, 0, 0 | 0 | −13% |
| 5 | VT-1 0.009 ug/mouse | 5 | 29, 41, 34, 29, 21 | 30.8 | +5% |
| 6 | VT-1 0.036 ug/mouse | 5 | 7, 16, 29, 16, 6 | 14.8 | +5% |
| 7 | VT-1 0.144 ug/mouse | 5 | 1, 4, 2, 3, 1 | 2.2 | +5% |
| EXPT 2 | | | | | |
| 1 | Control | 4 | 15, 12, 8, 12 | 11.75 | <5% |
| 2 | ACP-2 ug/mouse | 5 | 0, 1, 0, 0, 0 | 0.2 | <5% |
| 3 | VT-1 0.1 ug/mouse | 4 | 0, 0 | 0 | <5%*** (2 deaths) |
| 4 | VT-1B-0.2 ug/mouse | 5 | 13, 14, 9, 7, 19 | 12.4 | <5% |
| 5 | VT-1B-10 ug/mouse | 5 | 8, 3, 9, 11 | 6.8 | <5% |

Mice were treated with VT-1 or ACP(1-p) I day after cell injection (1000 KHT cells/mouse i-v).
Lung nodules counted @ 20 days after cell injection.
*Mean change in gp wi-max during 10 days (Expl 1) or 4 days (Expt 2) after VT-1 or ACP injection. Max wt loss @ days 7–8.
**Death occurred @ days 2–3 after ACP injection
***Deaths occurred @ days 7–8

Purified VT1 was found to mimic the anti-metastatic effect of ACP on the growth of this tumour from a primary subcutaneous site. Lung metastasis was completely inhibited. Moreover, prior immunization of mice with the purified B-subunit of verotoxin completely prevented any protective effect of ACP when the animals were subsequently treated with the tumour and ACP (Table 2).

Figure 3:
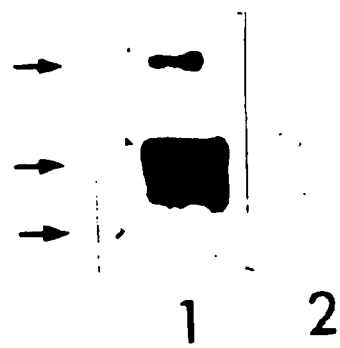
FIG. 3 represents VT1 contained within ACP preparation binding to $Gb_3$ (and $Gb_2$).

ACP was tested for glycolipid binding by TLC overlay using monoclonal anti-VT1 or anti-VT2c. Anti-VT1 shows extensive binding of a component within the ACP preparation to globotriaosylceramide and galabiosyl ceramide (FIG. 3). This binding specificity is identical to that reported for purified VT1(8). No binding component reactive with anti-VT2 was detected. In FIG. 3 anti VT antibodies were used

TABLE 2

Response of KHT lung nodules, growing to immunized mice, to treatment with VT1 or ACP.

| GP | IMMUNI- ZATION* | TREATMENT | # OF MICE | # OF LUNG NODULES/MOUSE | MEAN | WT LOSS/ GAIN* |
|---|---|---|---|---|---|---|
| 1 | None | None | 6 | 34, 47, 53, 62, 43, 52 | 48.5 | <5% |
| 2 | None | VT-1 −0, 2 ug/mouse | 5 | | | 5 deaths (dy 6–8)** |
| 3 | None | ACP-2.0 ug/mouse | 5 | 0, 1, 2, 0, 0 | 0.6 | −8% |
| 4 | VT-1B + FA | None | 5 | 43, 40, 47, 43, 23 | 39.2 | −6% |
| 5 | VT-1B + FA | VT-1 −0, 2 ug/mouse | 6 | 26, 44, 49, 21, 43, 37 | 36.7 | <5% |
| 6 | VT-1B + FA | ACP-2.0 ug/mouse | 6 | 50, 38, 33, 41, 48, 50 | 43.3 | <5% |
| 7 | FA only | None | 5 | 44, 60, 19, 25, 40 | 37.6 | <5% |
| 8 | FA only | VT-1 −0, 2 ug/mouse | 5 | | | 5 deaths (dy 6–8)*** |
| 9 | FA only | ACP −2.0 ug/mouse | 5 | 1, 1, 2, 1, 0 | 1 | −6% |

Mice were treated with VT-1 or ACP(i-p) 1 day after cell injection (1000 KHT cells/mouse).
Lung nodules counted @ 20 days after cell injection (i-v).
*Immunization was 2 injections of VT-1B (10 ug/mouse +/− Freund's Adjuvant (FA) given (i-p) 4 weeks and 2 weeks before cell injection.
**Mean change in gp wt - max during 13 days. Maximum weight loss @ day 7–8.

to detect binding to the immobolized glycolipids. Arrows indicate position of standard (from the top) galabiosyl ceramide, globotriaosyl ceramide and globotetraosyl ceramide. Panel 1-detection using anti VT1, panel 2-detection using anti VT2c.

Figure 5:
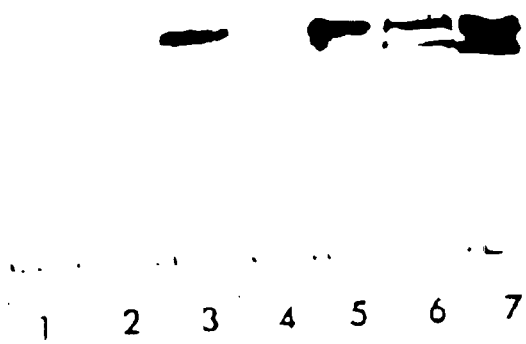
FIG. 5 represents VT thin layer chromatography overlay of selected cell line glycolipids.
Figure 6:
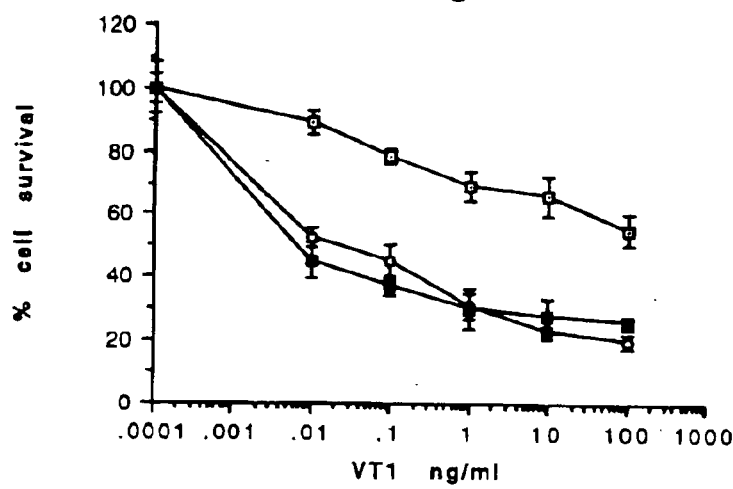
FIG. 6 represents in three graphs ovarian cell line sensitivity to VT1, VT2 and VT2c.
Figure 6:
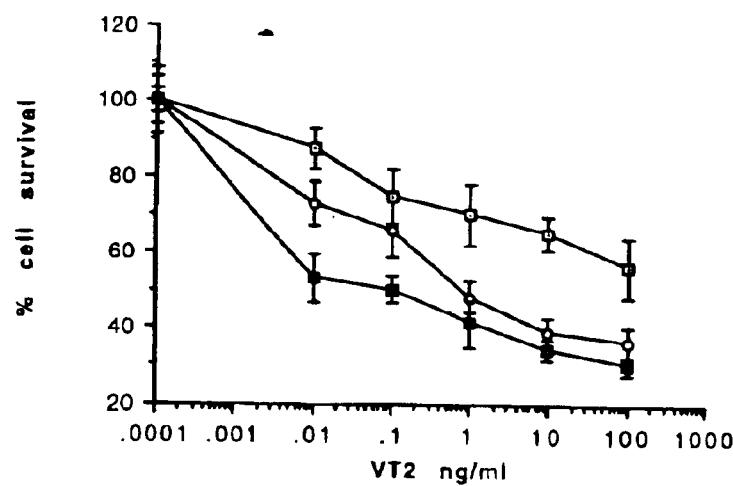
Figure 6:
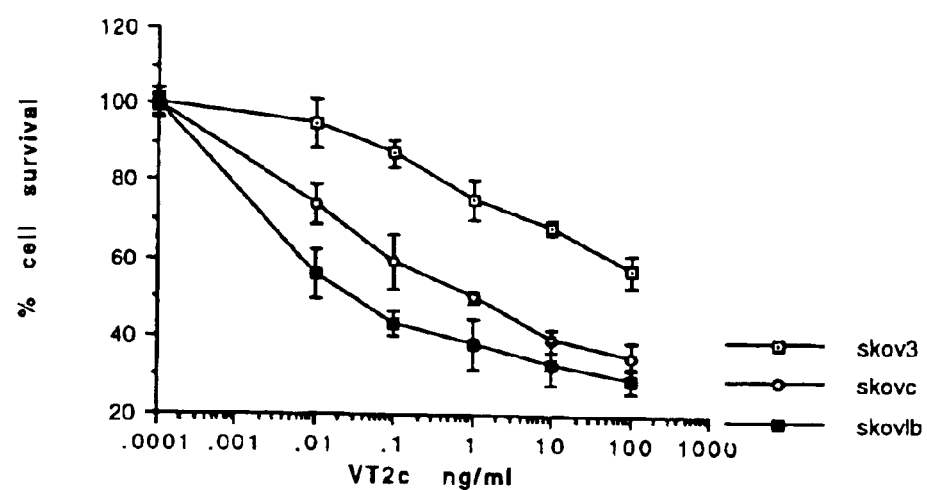
Figure 7:
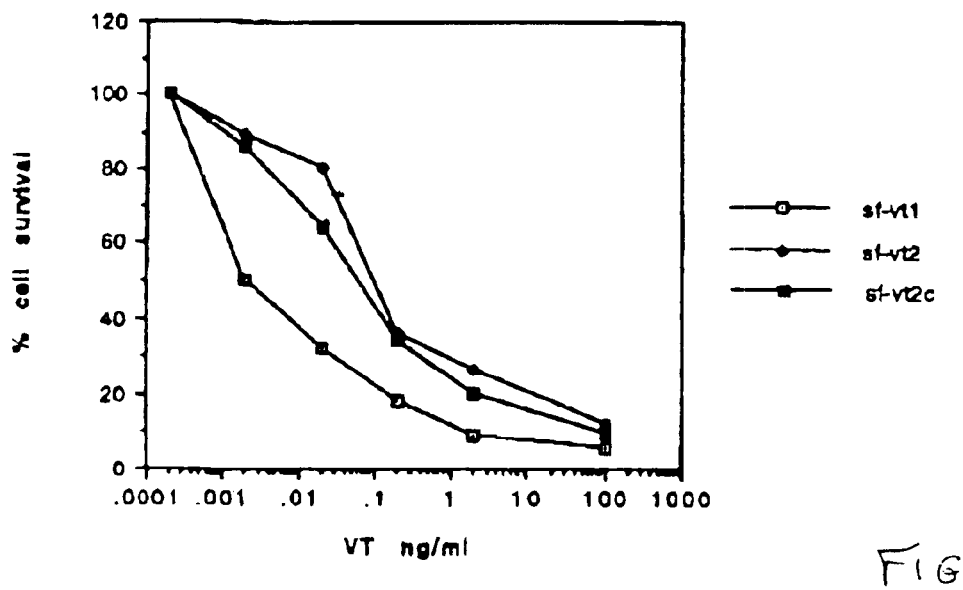
FIG. 7 represents glioblastoma multiforme cell line sensitivity to VT1, VT2 and VT2c.
Figure 8:
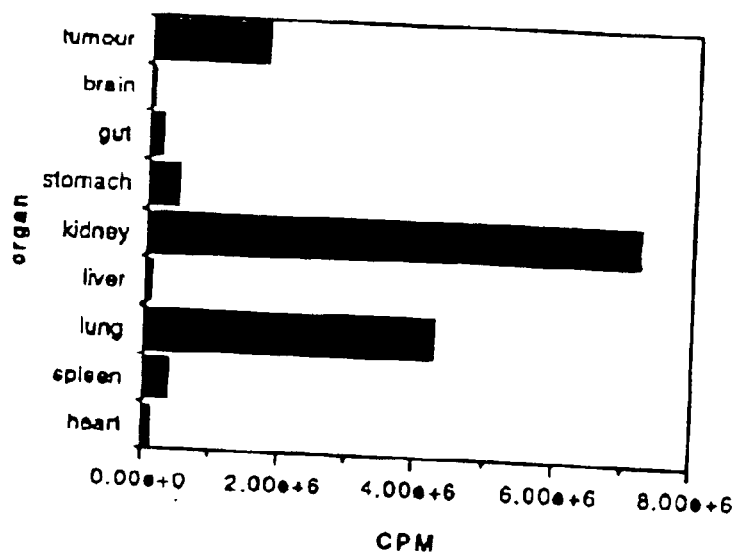
FIG. 8 represents the distribution of labelled VT1 B subunit (VTB-$^{131}$I) administered IP (inter-peridinually) in a $Gb_3$ tumour bearing nude mouse.

VT1 demonstrated in vitro activity against a variety of ovarian carcinoma cell lines. A large number of primary human ovarian tumour biopsies were screened for the expression of $Gb_3$ via TLC overlay using purified VT1. It was found that $Gb_3$ was barely detectable in normal ovary tissue, whereas in all cases a significant increase in expression of $Gb_3$ was observed in the ovarian carcinoma. Similarly, elevated levels of $Gb_3$ were found in acites tumour and in tumours that had metastized to the omentum, (FIG. 4) which defines lane 1, ovarian omentum metastasis; lane 2: tumour biopsy; lane 3, tumour biopsy; lanes 3–6, normal ovary; lane 7, human kidney $Gb_3$ standard. Surprisingly, we have found that multi-drug resistant variants of ovarian tumour cell lines were considerably more sensitive to VT1 cytotoxicity than the drug sensitive parental cell line (FIGS. 2, 5 and 6). Similar effects had been observed for ACP. FIG. 2 shows human ovarian tumour cell lines sensitive to ACP tested for VT sensitivity. Human ovarian and breast tumour derived cell lines were tested for VT1 sensitivity wherein ovarian 1, 2, 3, 4 and 5 are denoted □, +, x, ■ and o respectively, and breast-SKBR3Δ, 468♦, 453●, 231▲. The cell lines 1-ovarian, 453 and SKBR3, previously shown to be resistant to ACP, were also resistant to up to 20 ng/ml VT1.

The 1, 2, 3 and 4 cells were from ovarian cancer patients; the 453 cells were from a breast cancer patient; 231 and SKBR3 are breast adenocarcinoma cell lines, and 5, SKOV3 and SKOVLB are adenomacarcinous ovarian cancer cell lines. The lines 1, 453 and SKBR3, resistant to ACP, were co-resistant to VT1. FIG. 5 shows VT sensitive and resistant cell lines tested for the presence of $Gb_3$ by VT binding in tlc overlay. Glycolipid from an equal number of cells were extracted and separated by tlc prior to toxin binding. In FIG. 5, lane 1:SKBR3, lane 2:468, lane 3:231, lane 4:453, lane 5 $Gb_3$ standard, lane 6:SKOV3, lane 7:SKOVLB. Cell lines SKBR3, 468, 231 and 453 are derived from breast tumours. Only 231 is sensitive to VT1. SKOVLB is a multiple drug resistant ovarian tumour cell line derived from SKOV3.

Figure 4:
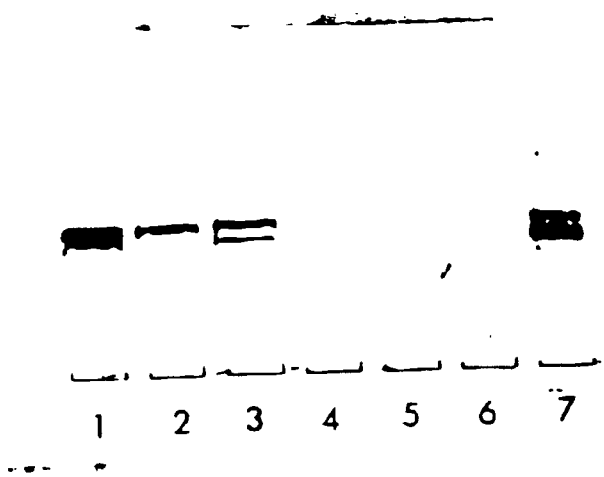
FIG. 4 represents VT thin layer chromatography overlay of ovarian tumour and ovary glycolipids.

Ovarian tumour cells were highly sensitive to VT (FIG. 3) and contained elevated levels of the VT receptor, $Gb_3$ (FIG. 4). Breast cancer cells were for the most part, toxin resistant (FIG. 3) and receptor negative (FIG. 5). Low levels of $Gb_3$ were detected in normal ovarian tissue but these were markedly elevated for the ovarian tumour tissue samples.

The specific elevation of $Gb_3$ in ovarian tumours as opposed to normal ovary tissue provides the feasibility of using the toxin in the management of this malignancy. Ovarian tumours are often refractory to chemotherapy and prognosis is poor. Indeed, preliminary phase 1 clinical trials using a ACP injected directly into skin malignancies (Mycosis fungoides) have proven successful without adverse systemic effects.

With reference now to FIG. 6, human derived ovarian tumour cell lines were tested for VT1, VT2, and VT2c sensitivity. The cells were grown to confluence in 48-well plates, then incubated for 48 hrs. in the presence of increasing doses of VTs. SKOVLB, the multiple drug resistant variant of SKOV3 ovarian line, showed the most sensitivity to VT's with SKOVLC being the next most sensitive to the VT's.

We have found that both drug resistant cells are approximately 500 to 1000 times more sensitive to verotoxin cytotoxicity than the parental SKOV3 cell line.

FIG. 7 shows the effect after 48 hrs. of treatment of the brain tumour SF-539 cell line derived from a recurrent, right temporoparictal glioblastoma multiform with VT1, VT2, and VT2c. This cell line, as others, was highly sensitive to VT's.

FIG. 8 provides the results from imaging a nude mouse with $^{131}$I-VT1B (CPM distribution in different organs). VT1B-$^{131}$I cpm distribution in nude mouse with implanted ovarian tumour showed that a considerable amount of radiolabled VT1B had been concentrated in the ovarian tumour. Only a trace amount of VT1B was located in the brain where the potential VT1 side effect was considered. Since the lung in human adult is not the site of concern for VT1 toxicity this does not present a problem for treatment of human adult with ovarian tumour. In addition the CPM in kidney includes the excreted radiolabelled VT1 B subunit. Accordingly, based on this test, imaging with labelled VT1 B subunit can be a very useful method for screening the susceptible patient to VT1 cytotoxicity.

FIG. 9 shows the sensitivity of a variety of human astrocyta cell lines to VT1. All these cells contain $Gb_3$ but show variable sensitivity to VT1 induced cytotoxicity. This suggests that certain astrocytomas will be susceptible to verotoxin wheres others may not. This is important since astrocytomas are very refractory to treatment at the present time and cell sensitivity in vitro to concentrations as low as 5 ng per/ml is rare.

While the invention has been described in detail and with reference to specific embodiments thereof, it will be apparent to one skilled in the art that various changes and modifications can be made therein without departing from the spirit and scope of the invention.

We claim:

1. A method for killing cancer cells from a patient, comprising obtaining said cells from said patient, contacting said cells with a verotoxin, such that said cells are killed, wherein said cells are $Gb_3$ positive and multidrug resistant.

2. The method of claim 1, wherein said cells are contacted with said verotoxin in vitro.

3. A method for killing $Gb_3$ positive cells from a breast, ovarian, brain, or skin tumor in a patient, comprising obtaining said cells from said patient, contacting said cells with a verotoxin, such that said cells are killed.

4. The method of claim 3, wherein said cells are contacted with said verotoxin in vitro.

5. The method of claim 3, wherein said cells are multidrug resistant.

* * * * *